(12) United States Patent
Suzuki et al.

(10) Patent No.: US 8,933,252 B2
(45) Date of Patent: Jan. 13, 2015

(54) METHOD FOR RAPID FLUOROMETHYLATION AND METHOD FOR PREPARATION OF PET TRACER USING THE SAME

(75) Inventors: Masaaki Suzuki, Kobe (JP); Hisashi Doi, Kobe (JP); Miki Goto, Kobe (JP)

(73) Assignee: Riken, Wako-Shi (JP)

(*) Notice: Subject to any disclaimer, the term of this patent is extended or adjusted under 35 U.S.C. 154(b) by 0 days.

(21) Appl. No.: 13/513,565

(22) PCT Filed: Dec. 3, 2010

(86) PCT No.: PCT/JP2010/071632
§ 371 (c)(1),
(2), (4) Date: Jul. 30, 2012

(87) PCT Pub. No.: WO2011/068181
PCT Pub. Date: Jun. 9, 2011

(65) Prior Publication Data
US 2012/0289716 A1 Nov. 15, 2012

(30) Foreign Application Priority Data
Dec. 4, 2009 (JP) ................................. 2009-277028

(51) Int. Cl.
*C07C 67/343* (2006.01)
*C07D 311/30* (2006.01)
*A61K 51/04* (2006.01)
*C07B 59/00* (2006.01)

(52) U.S. Cl.
CPC .............. *C07D 311/30* (2013.01); *A61K 51/04* (2013.01); *A61K 51/0421* (2013.01); *C07B 59/001* (2013.01); *C07C 67/343* (2013.01); *C07B 2200/05* (2013.01)
USPC ......................................... 549/403; 560/103

(58) Field of Classification Search
USPC ......................................... 549/403; 560/103
See application file for complete search history.

(56) References Cited

U.S. PATENT DOCUMENTS 8,288,604 B2 * 10/2012 Suzuki et al. ................ 585/446
2004/0171833 A1 9/2004 Buchwald et al.
2010/0249477 A1 9/2010 Suzuki et al.

FOREIGN PATENT DOCUMENTS

| JP | 2006-509046 A | 3/2006 |
| WO | WO-2004/052939 A2 | 6/2004 |
| WO | WO-2007/046258 A1 | 4/2007 |
| WO | WO-2008/023780 A1 | 2/2008 |

OTHER PUBLICATIONS

Doi, H. et al., "Palladium(0)-Mediated Rapid Methylation and Fluoromethylation on Carbon Frameworks by Reacting Methyl and Fluoromethyl Iodide with Aryl and Alkenyl Boronic Acid Esters: Useful for the Synthesis of [$^{11}$C]CH$_{3-C-and}$[$^{18}$F]FCH$_2$—C-Containing PET Tracers," Chem. Eur. J., vol. 15, pp. 4165-4171 (2009).
Zhang, M. et al., "[$^{18}$F]Fluoromethyl iodide ([$^{18}$F]FCH$_2$I): preparation and reactions with phenol, thiophenol, amide and amine functional groups," J. of Fluorine Chem., vol. 125, pp. 1879-1886 (2004).
Siméon, F.G. et al., "Synthesis and Simple $^{18}$F-Labeling of 3-Fluoro-5-(2-(2-(fluoromethyl)thiazol-4-yl)ethynyl)benzonitrile as a High Affinity Radioligand for Imaging Monkey Brain Metabotropic Glutamate Subtype-5 Receptors with Positron Emission Tomography", J. Med. Chem., vol. 50, pp. 3256-3266 (2007).
Zheng, L. et al., "Synthesis of [$^{18}$F]fluoromethyl iodide, a synthetic precursor for fluoromethylation of radiopharmaceuticals," Applied Radiation and Isotopes, vol. 52, pp. 55-61 (2000).

* cited by examiner

*Primary Examiner* — Noble Jarrell
*Assistant Examiner* — John Mauro
(74) *Attorney, Agent, or Firm* — Birch, Stewart, Kolasch & Birch, LLP

(57) ABSTRACT

Provided are: a method for rapid fluoromethylation, by which a fluoromethyl group can be easily bonded to an aromatic-ring carbon of an aromatic compound with little generation of by-products; and a process for preparation of a PET tracer using the same. The method is characterized by cross-coupling an organoboron compound in which an aromatic ring is bonded to a boron atom with FCX$_2$Br (wherein X is ordinary hydrogen or heavy hydrogen) in a solvent obtained by adding water to an aprotic polar solvent, in the presence of a palladium complex, a phosphine ligand, and a base.

16 Claims, 11 Drawing Sheets

METHOD FOR RAPID FLUOROMETHYLATION AND METHOD FOR PREPARATION OF PET TRACER USING THE SAME

This nonprovisional application claims is the national stage of International Application No. PCT/JP2010/071632 filed in Japan on Dec. 3, 2010. This application also claims priority under 35 USC §119(a)-(d) of Japanese Application No. JP 2009-277028, filed in the JPO on Dec. 4, 2009.

TECHNICAL FIELD

The present invention relates to a rapid methylation method for carrying out fluoromethylation of an aromatic compound in a short time. The present invention can be preferably used in synthesis of a radioactive tracer, which is a key to positron-emission tomography (hereinafter referred to as "PET").

BACKGROUND ART

The PET method is a method in which a labeled compound that is labeled with a short-lived radioactive nucleus discharging positrons (hereinafter referred to as a "tracer") is administered into a living body and the γ ray generated from this tracer is measured with a PET camera (detector constituted with a γ ray scintillator and a photoelectron multiplier) to thus image the distribution in the living body with a computer. This PET method is used in specification of a tumor site such as a cancer cell as a nuclear medicine examination, diagnosis of Alzheimer's disease, cerebral infarction and the like, diagnosis of mental diseases such as depression and evaluation of treatments, drug kinetics and evaluation of drugs.

Examples of short-lived radial nuclear species frequently used in the PET method include [$^{11}$C] and [$^{18}$F].

Among them, the tracer labeled with [$^{11}$C] has an advantage of having an extremely wide applicable range because of utilizing a carbon atom present in all organic compounds. However, since the half-life period of [$^{11}$C] is only about 20 minutes, it has been assumed that a labeling reaction by [$^{11}$C] should be carried out within 40 minutes (within twice of the half-life period) until synthesis, purification, and administration into a living body. Regardless of such difficulties, the present inventors have developed rapid C-[$^{11}$C]methylation reaction of various aromatic compounds and aryl compounds so far (for example, Patent Documents 1 and 2). The development enables a [$^{11}$C]methylation reaction into the basic skeleton (in the carbon nucleus) of a compound due to a carbon-carbon bonding method. Therefore, as compared to a conventional [$^{11}$C] methylation method on a hetero atom, it is expected that the labeled site is more stable for chemical and biological metabolism, and the method becomes a significantly powerful research means for drug discovery.

On the other hand, the half-life period of [$^{18}$F] (110 minutes) is 5 time or more as compared to the half-life period of [$^{11}$C] (20 minutes), and there is an advantage such that a time for preparation of a PET tracer and a time for PET diagnosis can be extended. In addition, when two PET tracers labeled with [$^{11}$C] and [$^{18}$F] to one desired compound can be realized, effective application of the difference of the half-life periods can be used as an extremely useful method for drug kinetics in a living body and an analysis of a metabolic product of the desired compound.

Therefore, the present inventors have developed a rapid C-[$^{18}$F]fluoromethylation reaction of various aromatic compounds so far, in addition to development of the rapid C-[$^{11}$C] methylation reaction (Patent Document 2). Patent Document 2 discloses that a coupling reaction of methyl fluoroiodide and a phenyl boronic acid pinacol ester progresses in a reaction time of only 5 minutes at a yield of 57%, as shown in the reaction formula below. This reaction can be classified as a kind of suzuki-miyaura cross coupling, and the coupling reaction is an innovative reaction from the viewpoint that SP$^3$ carbon can be bonded to an aromatic ring.

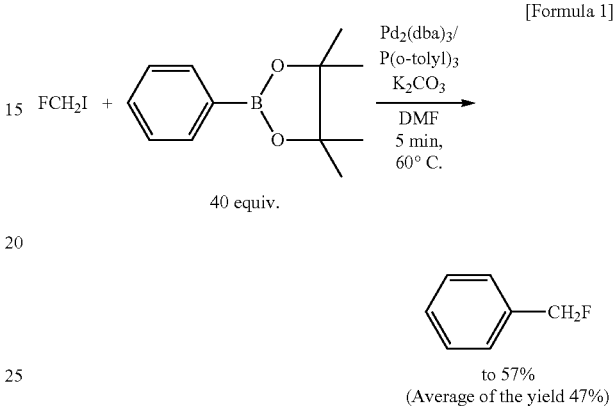

[Formula 1]

PRIOR ART DOCUMENTS

Patent Documents

Patent Document 1: WO2007/046258
Patent Document 2: WO2008/023780

DISCLOSURE OF INVENTION

Problems to be Solved by the Invention

However, since [$^{18}$F]FCH$_2$I is chemically unstable in the bonding reaction of [$^{18}$F]FCH$_2$I to a benzene ring, which is described in the above Patent document 2, the reaction should be promptly carried out by a skilled lab technician, otherwise there has been a problem such that the reaction can be hardly succeeded.

In addition, there has been also a problem such that in the bonding reaction of [$^{18}$F]FCH$_2$I to an aromatic ring, a considerable amount of by-products is generated other than a desired compound.

For example, as shown in the reaction formula (Formula 2) below, when [$^{18}$F]FCH$_2$I and benzoic acid ester (1) in which pinacol borane was substituted to the para position were cross-coupled, the reaction was even performed at 65° C. for 5 minutes in a DMF solvent that was considered to be an optimal condition, in the presence of K$_2$CO$_3$, using a Pd complex of Pd$_2$(dba)$_3$/P(o-CH$_3$C$_6$H$_5$)$_3$ (1:6), as shown in FIG. 1, which resulted in generating a considerable amount of by-products (peak existing within the retention time from 1.0 to 4.5 minutes), and the yield of the desired 4-[$^{18}$F]fluorobenzoic acid methyl ester (2) found from HPLC was as low as 23%.

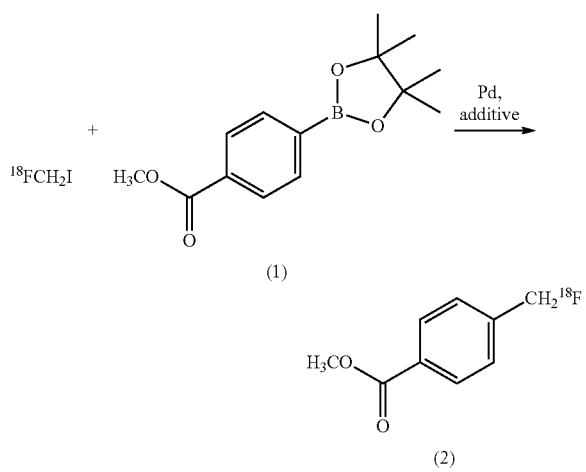

(1)

(2)

The present invention was made in view of the above described conventional circumstances, and a problems to be solved by the invention is to provide a method for rapid fluoromethylation, by which a fluoromethyl group can be easily bonded to an aromatic-ring carbon of an aromatic compound with little generation of by-products, and a process for preparation of a PET tracer using the same.

Means for Solving the Problems

In order to solve the above described problems, the inventors considered using $FCH_2Br$ in place of chemically unstable $FCH_2I$ in a model reaction of the reaction formula (Formula 2) described above. However, in the case of carrying out the method of claim 1 in Patent Document 2 using $FCH_2Br$ (that is, in the case that an organoboron compound in which an aromatic ring is bonded to boron are cross-coupled with $FCH_2Br$ in an aprotic polar solvent in the presence of a palladium complex, a phosphine ligand, and a base), the problem of generating a large amount of by-products could not be solved.

Therefore, as a result of further intensive studies, surprisingly, the inventors found that use of a solvent obtained by adding water to an aprotic polar solvent made it possible to significantly decrease a generation amount of by-products and accomplished the present invention.

That is, the method for rapid fluoromethylation of the present invention is characterized by cross-coupling an organoboron compound in which an aromatic ring is bonded to a boron atom with $FCX_2Br$ (wherein X is ordinary hydrogen or heavy hydrogen) in a solvent obtained by adding water and/or an alcohol to an aprotic polar solvent, in the presence of a palladium complex, a phosphine ligand, and a base.

The method for rapid fluoromethylation of the present invention is considered to proceed in the following reaction mechanism (hereinafter, the method will be described assuming that X is hydrogen, but the case of using heavy hydrogen is also the same).

That is, firstly, a stereoscopically bulk phosphine ligand coordinates to a palladium complex in an unsaturated manner to generate an active reaction field. Then, $FCH_2Br$ is further oxidatively added to the palladium complex to which the phosphine ligand coordinated to form a divalent palladium complex in which the phosphine ligand coordinated to $FCH_2PdBr$.

On the other hand, a base coordinates to a boron atom of an organoboron compound in which an aromatic ring is bonded to the boron atom and a boron ate complex having increased polarity between boron and carbon is formed.

Then, a metal exchange reaction is generated between the divalent palladium complex in which the phosphine ligand coordinates and the boron ate complex, and further, Br is detached to form a more stable boron ate complex. Finally, a reductive elimination reaction occurs and a compound in which a fluoromethyl group is bonded to an aromatic compound is obtained.

In addition, the palladium complex is preferably in a state of an electron rich 0-valent state in order to oxidatively add $FCH_2Br$. Therefore, it is advantageous to carry out a reaction using a 0-valent palladium complex, but a method of using a divalent palladium complex and reducing in a reaction system to form into a 0-valent state or a method of directly using a divalent palladium complex to initiate a reaction may also be used.

Next, functions of water added to the solvent in the method for rapid fluoromethylation of the present invention will be described.

The present inventors initially presumed that an aprotic polar solvent coordinates to a vacant orbital of a palladium atom in a palladium complex that is generated in the middle of the reaction, thereby reducing instability of the palladium complex, and side reactions such as degradation can be minimized. If this presumption is correct, it is a common knowledge for a specialist in the same field to consider that presence of water that is a protic polar solvent hinders coordination of an aprotic polar solvent and thus is not preferable for progress of the reaction. The fact is that when water was added to an aprotic polar solvent, reactivity of the fluoromethylated product that is the desired compound decreased. However, a surprising result that has been never expected by the present inventors was obtained by addition of water. That is, the unexpected result such as significantly decreasing generation of by-products by addition of water to an aprotic polar solvent was revealed from results of an analysis made by HPLC.

Details of the function of water have not been clarified yet but can be presumed as follows.

When fluoromethylation is carried out without adding water to an aprotic polar solvent, a fluoroboric acid ester having a thermodynamically stable boron-fluorine bond is considered to be generated as a by-product. Details of the reaction mechanism of generation is indefinite but the reason is presumed that a fluorine ion is detached from $FCH_2Br$ being the raw material and bonded to a boron atom. Further, the fluoroboric acid ester being the by-product is subjected to degradation in the presence of a base and other by-products may be possibly generated. Therefore, many by-products are observed in HPLC, and at the same time, a yield of a fluoromethylated product that is a desired compound is assumed to decrease.

On the other hand, it is presumed in the method for rapid fluoromethylation of the present invention in which water is added to an aprotic polar solvent that generation of fluoroboric acid ester having a boron-fluorine bond is suppressed and a boric acid compound that is a more thermodynamically stable compound due to a boron-oxygen bond is generated. According to experimental results by the present inventors, addition of water induced reduction in reactivity, but a generation ratio of by-products significantly decreased. The problem of reduction in reactivity could be solved by increasing a reaction temperature. As a result, according to the method for rapid fluoromethylation of the present invention, generation of by-products can be suppressed, a yield is preferable, and the method can be also preferably used as a process for preparation of a $^{18}$F-labeled PET tracer.

Functions of water in the method for rapid fluoromethylation of the present invention were described above, and functions of an alcohol in the case of adding an alcohol to an aprotic polar solvent in place of water (or with water) is considered to be the same. This is because an alcohol is a protic polar solvent in the same manner as water and it can be presumed that generation of a fluoroboric acid ester having a boron-fluorine bond is suppressed and a boric acid compound that is a more thermodynamically stable compound due to a boron-oxygen bond is generated.

A kind of an alcohol is not particularly limited, and examples thereof include methyl alcohol, ethyl alcohol, butyl alcohol, and isopropyl alcohol.

$FCD_2Br$ (D denotes heavy hydrogen) can also be used in place of $FCH_2Br$ as the fluorine source in the method for rapid fluoromethylation of the present invention. Chemical reactivity of $FCD_2Br$ is not so different from chemical reactivity of $FCH_2Br$, and therefore, $FCD_2Br$ can be used as the fluorine source in the method for rapid fluoromethylation in the same manner. In addition, findings regarding more detailed kinetics in a living body can be obtained by comparison of kinetics in living bodies introduced with a $FCD_2$ group and introduced with a $FCH_2$ group.

In the second aspect of the present invention, a value of (water content)/(aprotic polar solvent content) is 0.02 or more and 10 or less. When the value of (water content)/(aprotic polar solvent content) is less than 0.02, an effect of decreasing generation of by-products is reduced. When the value of (water content)/(aprotic polar solvent content) exceeds 10, solubility of a substrate is deteriorated and there is fear that a reaction in a homogeneous system is difficult. The value of (water content)/(aprotic polar solvent content) is particularly preferably 0.03 or more and 1 or less and the most preferably 0.05 or more and 0.15 or less.

In the third aspect of the present invention, $FCX_2Br$ (wherein X is ordinary hydrogen or heavy hydrogen) is labeled with $^{18}$F. Accordingly, a compound obtained in the method for rapid fluoromethylation of the present invention can be used as a PET tracer. Further, since $^{18}$F has such a long half-life period as 110 minutes, time latitude for further converting a PET tracer labeled with $^{18}FCX_2$ into another compound is generated. Therefore, when a PET tracer labeled with $^{18}FCX_2$ is bonded to a substance, for example, an enzyme, an antigen, an antibody, or the like, in a click reaction and a PET image is taken, a distribution of an enzyme protein, a distribution of a receptor of an antigen, and a distribution of an antibody, which are labeled in the click reaction, are imaged. Such imaging can give important research tools for biochemical researches such as activity of an enzyme and clarification of an antigen-antibody reaction.

In the fourth aspect of the present invention, the organoboron compound in which an aromatic ring is bonded to a boron atom is an aromatic boronic acid ester. The present inventors confirm obtaining addition of a fluoromethyl group to an aromatic compound promptly at a high yield by using an aromatic boronic acid ester as the organoboron compound.

A pinacol ester is preferable for the aromatic boronic acid ester. Accordingly, in a reductive elimination reaction in the final step of the method of rapid methylation of an aromatic compound of the present invention, pinacol borate having high polarity is generated. Therefore, when a desired substance is separated and generated from a reaction solution by reversed liquid chromatography, or the like, a retention time of pinacol borate having high polarity is shorter than retention times of the desired substance and the starting substrate remained in a large amount, and separation can be thus more completely performed.

In the fifth aspect of the present invention, the base is a carbonate salt. The inventors confirm surely obtaining addition of a fluoromethyl group to an aromatic compound promptly at a high yield by using a carbonate salt as the base.

In the sixth aspect of the present invention, the phosphine ligand is tri-o-tolylphosphine. The inventors confirm progressing fluoromethylation promptly at a high yield by using tri-o-tolylphosphine. The reason thereof is assumed to be because bulkiness of tri-o-tolylphosphine forms a reaction field with high activity. What is more, tri-o-tolylphosphine has an advantage of being a stable crystalline compound in the air and easily handled, as compared to (di-tert-butyl) methylphosphine.

In the seventh aspect of the present invention, the palladium complex is tris(dibenzylideneacetone)dipalladium(0). The inventors confirm progressing methylation promptly at a high yield by using the palladium complex. Particularly preferably, a palladium complex is tris(dibenzylideneacetone)dipalladium(0), and a phosphine ligand is tri-o-tolylphosphine. Therefore, in the eighth aspect of the present invention, the palladium complex is tris(dibenzylideneacetone)dipalladium(0), and the phosphine ligand is tri-o-tolylphosphine.

In the ninth aspect of the present invention, each of an organoboron compound in which an aromatic ring, an alkenyl group or an alkynyl group is bonded to a boron atom, a palladium complex, a phosphine ligand, and a base is used in an equivalent amount or more with respect to $FCX_2Br$ (wherein X is ordinary hydrogen or heavy hydrogen). Accordingly, a desired compound can be obtained at a high yield.

Particularly, in order to obtain the desired compound at a high yield, the added amount of the phosphine ligand is preferably twice or more with respect to a Pd amount contained in the added palladium complex in a molar ratio. Therefore, in the tenth aspect of the present invention, the added amount of the phosphine ligand is twice or more of a Pd amount contained in the added palladium complex in a molar ratio. A more preferable amount is 2.5 times or more, and the most preferable amount is 3 times or more.

A fluoromethylated product obtained with the method for rapid fluoromethylation of the present invention can be used as a PET tracer.

That is, the process for preparation of a PET tracer of the present invention is characterized in that an organoboron compound in which an aromatic ring is bonded to a boron atom is cross-coupled with [$^{18}$F]$FCX_2Br$ (wherein X is ordinary hydrogen or heavy hydrogen) in a solvent obtained by adding water and/or an alcohol to an aprotic polar solvent in the presence of a palladium complex, a phosphine ligand, and a base.

Effect of the Invention

As described above, according to the method for rapid fluoromethylation of the present invention, a fluoromethyl group can be easily bonded to an aromatic-ring carbon of an aromatic compound with little generation of by-products.

BEST MODE FOR CARRYING OUT THE INVENTION

An aprotic polar solvent used in the method for rapid fluoromethylation of the present invention is not particularly limited, and examples that can be used include N,N'-dimethylpropylene urea (DMPU), N,N'-dimethylformamide (DMF), N-methyl-2-pyrrolidone (NMP), dimethyl sulfoxide (DMSO), sulfolane, N,N'-dimethylacetamide (DMA), and N,N'-dimethylimidazolidinone. In addition, ethers such as diethyl ether, dibutyl ether, tetrahydrofuran, 1,4-dioxane, and diisopropyl ether, glymes such as monoglyme, diglyme, triglyme and tetraglyme, and nitriles such as acetonitrile and adiponitrile can also be used.

Examples of the organoboron compound in which an aromatic ring is bonded to a boron atom include boronic acid and boronic acid esters (also including various cyclic or acyclic boronic acid esters). In addition, a kind of the aromatic ring in the organoboron compound in which an aromatic ring is bonded to a boron atom is not particularly limited, and an aromatic ring having a heterocyclic ring can also be used.

Furthermore, the palladium complex is not particularly limited, and examples thereof include $Pd_2(dba)_3$, $PdCl_2(dppf)_2$, $Pd(PPh_3)_4$, and $PdCl_2(PPh_3)_2$.

A phosphine ligand in the present specification is not particularly limited as long as it is a compound that catalyzes the reaction of the present invention, examples thereof include all compounds that are serially changed in electronic and stereoscopic effects as a ligand according to a kind of a substituent bonded to a P atom, other than tri-o-tolylphosphine and (di-t-butyl)methylphosphine, which is a concept including a bidentate ligand, a multidentate ligand and an asymmetric chelate ligand.

The base is not particularly limited, and examples such as carbonate salts of alkali metals, phosphate salts of alkali metals, and fluorides of alkali metals can be used.

Hereinafter, examples specifying the present invention will be described in detail as compared to comparative examples.

Example 1-1

In Example 1-1, p-[$^{18}$F]fluoromethyl benzoic acid methyl (2) was synthesized in DMPU:H$_2$O=9:1 (volume ratio) as a reaction solvent according to the following synthesis route (Formula 3). The detail thereof is shown below.

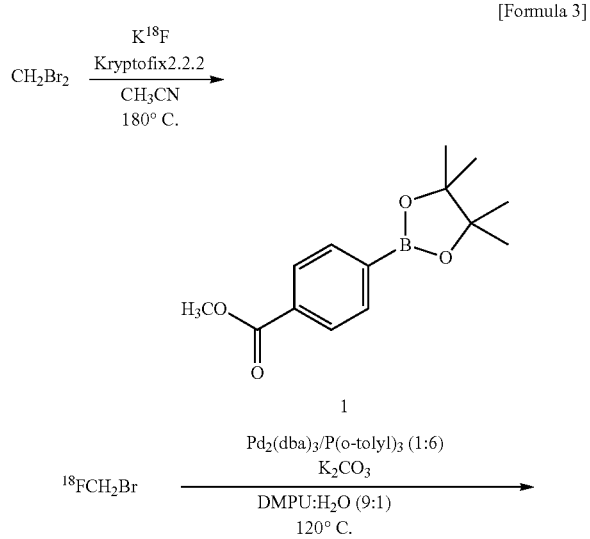

[Formula 3]

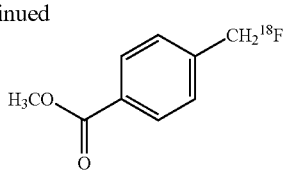

<Synthesis of [$^{18}$F]FCH$_2$Br>

Synthesis of [$^{18}$F]FCH$_2$Br that is the substrate of [$^{18}$F]fluoromethylation was carried out as follows using a labeling synthesis device (manufactured by JFE ENGINEERING CORPORATION.) shown in FIG. 2.

That is, water containing [$^{18}$F] fluorine ions was produced by irradiating 12 MeV electron beam (current value 30 μA, irradiation time 10 minutes) to [$^{18}$O] water (manufactured by TAIYO NIPPON SANSO CORPORATION, about 2 mL), using an accelerator cyclotron (HM-12S, manufactured by Sumitomo Heavy Industries, Ltd.) not shown. The thus obtained aqueous [$^{18}$O] solution containing about 10 GBq of [$^{18}$F]fluorine ions was transferred into the labeling synthesis device (manufactured by JFE ENGINEERING CORPORATION.) shown in FIG. 2, which was arranged in a hot cell not shown, and adsorbed to an anion exchange resin cartridge (Sep-Pak light Accell plus QMA Cartridges, manufactured by Waters). [$^{18}$F]KF was eluted into this cartridge through an aqueous acetonitrile solution (solution of acetonitrile:water=960 μL:40 μL, 1 mL) containing Kryptofix 222 (K.222) (95 mg) and potassium carbonate (17 mg) and added to the primary reaction container. This solution was heated at 180° C. under reduced pressure with flowing a N$_2$ gas and solidified with drying. Subsequently, acetonitrile (about 1 mL) was added to azeotropically dry remaining water. This azeotropic operation was carried out twice. An acetonitrile (1 mL) solution containing CH$_2$Br$_2$ (about 50 μL) was added to the obtained residue, and [$^{18}$F]FCH$_2$Br was synthesized with paying attention not to bumping under heating from 110° C. to 180° C. The gas evaporated under the heating was transferred into four-connected silica columns (Sep-Pak Plus Silica Cartridges) and adsorbed. Once again, an acetonitrile (from 0.5 mL to 1 mL) solution containing CH$_2$Br$_2$ (from 50 μL to 100 μL) was added to the reaction container and the same operation was carried out. In the same manner, CH$_2$Br$_2$ being the raw material, acetonitrile being the solvent, and the desired [$^{18}$F]FCH$_2$Br were separated through the above described four-connected silica columns and a porapak Type Q 80-100 mesh, while the evaporated gas was pushed away with a N$_2$ gas. Almost all of CH$_2$Br$_2$ being the raw material and acetonitrile being the solvent could be removed according to the operation. Note that the time for the serial operations of synthesis of [$^{18}$F]FCH$_2$Br was about 45 minutes until separation and purification of [$^{18}$F]FCH$_2$Br starting from supply of [$^{18}$F]F— with a cyclotron.

<Fluoromethylation Reaction>

Then, [$^{18}$F]FCH$_2$Br (about 500 MBq) was blown into 0.5 mL of a solution of DMPU:H$_2$O (9:1) that has been contained in the secondary reaction container in advance, and the obtained solution was transferred into the third reaction container containing organoboron compound 1 (32 μmol), Pd$_2$(dba)$_3$ (3.2 μmol), P(o-CH$_3$C$_6$H$_4$)$_3$ (19 μmol), and K$_2$CO$_3$ (3.6 μmol) and maintained at 120° C. and apart of the reaction solution was extracted after 5 minutes to carry out a HPLC analysis. HPLC analysis conditions: COSMOSIL AR-II 4.6× 150 mm column manufactured by NACALAI TESQUE, INC., column temperature at 30° C., eluate $CH_3CN:H_2O=45:55$, 1 mL/min flow rate, retention time of the desired product 2 for 6.5 to 7.5 minutes.

Example 1-2

In Example 1-2, the reaction time of the above described fluoromethylation reaction was set for 15 minutes. The other operations were the same as Example 1-1, and the explanation is thus omitted.

Example 1-3

In Example 1-3, the reaction time of the above described fluoromethylation reaction was set for 30 minutes. The other operations were the same as Example 1-1, and the explanation is thus omitted.

Examples 2-1, 2-2 and 2-3

In Examples 2-1, 2-2 and 2-3, the reaction temperatures of the above described fluoromethylation reactions were set at 90° C. The other operations were the same as Examples 1-1, 1-2 and 1-3, and the explanation is thus omitted.

Example 3

In Example 3, synthesis of a [$^{18}$F]fluoro(D$_2$) methylated product (4) of flavone that is a food component was carried out using the same reaction conditions as the case of Example 1-2 according to the following synthesis route (Formula 4) (D denotes heavy hydrogen). The details are shown below.

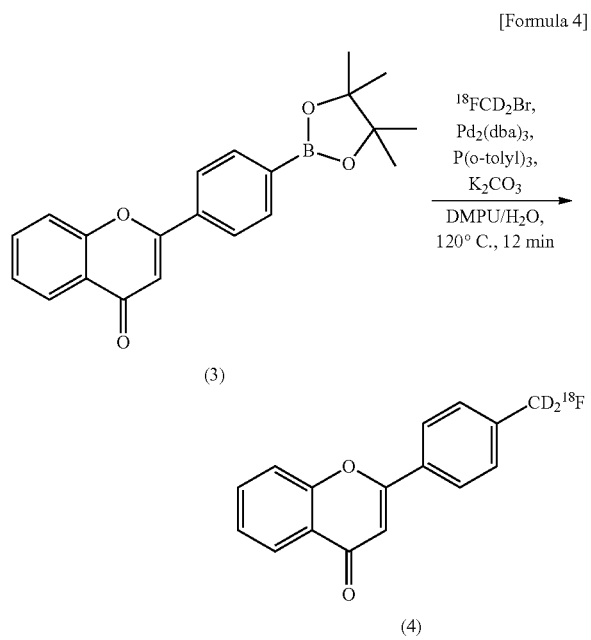

[Formula 4]

(3)

(4)

Synthesis of [$^{18}$F]FCD$_2$Br that is to be a substrate of [$^{18}$F]fluoro(D$_2$)methylation was carried out based on the method described in Example 1-1, using CD$_2$Br$_2$ in place of CH$_2$Br$_2$. About 30 GBq of [$^{18}$F]fluorine ion was reacted with CD$_2$Br$_2$, thereby synthesizing about 7 GBq of [$^{18}$F]FCD$_2$Br. This [$^{18}$F]FCD$_2$Br was blown into 0.5 mL of a solution of DMPU:H$_2$O (9:1) that has been contained in the secondary reaction container in advance, and the obtained solution was transferred into the third reaction container containing organoboron compound (3) of flavone (32 μmol), Pd$_2$(dba)$_3$ (3.2 μmol), P(o-CH$_3$C$_6$H$_4$)$_3$ (19 μmol), and K$_2$CO$_3$ (3.6 μmol) and reacted at 120° C. for 12 to 15 minutes. After completion of the reaction, the reaction solution was diluted with 1.0 mL of a washing liquid (solution of acetonitrile:water=3:2) and subsequently filtered with a cotton plug or a filter. The filtrate was supplied in preparative HPLC to thus separate the desired [$^{18}$F]fluoro(D$_2$) methylated product (4). The preparative column was COSMOSIL 5C18-AR-II 20 mm×250 mm, the preparative time, transfer layer, and flow rate are as follows.
(Preparative conditions)
(1) 0 to 7 minutes, $CH_3CN:H_2O=10:90$, 7 mL/min
(2) 7 to 10 minutes, $CH_3CN:H_2O=60:40$, 8 mL/min
(3) 10 to 20 minutes, $CH_3CN:H_2O=60:40$, 10 mL/min
(4) 20 to 35 minutes, $CH_3CN:H_2O=60:40$ to 65:35, 10 mL/min.

The obtained [$^{18}$F]fluoro(D$_2$)methylated product (4) was measured at a UV detection wavelength of 254 nm and with a γ ray detector; as a result, the retention time of the compound 4 was 21.9 minutes.

Further, a part of the reaction solution (20 μL) was supplied in analytical HPLC, and identification of the desired compound, a purity detection, and calculation of specific radioactivity were carried out. The analytical conditions are as follows.
(Analytical Conditions)

The analysis was made at a column temperature of 30° C., using the column of COSMOSIL 5C18-AR-II 4.6 mm×150 mm. The flow rate was 1 mL/min, and the transfer layer of $CH_3CN:H_2O=40:60$ was used. The reaction solution was measured at a UV detection wavelength of 254 nm with a γ ray detector; as a result, the retention time of the compound (4) was 15.7 minutes. The total radioactivity of the compound (4) was 0.6 GBq, the synthesis time was 88 minutes, the radiochemical purity was 99% or more, and an estimate value of the specific radioactivity was 400 GBq/μmol.

Comparative Examples 1-1, 1-2 and 1-3

In Comparative Examples 1-1, 1-2 and 1-3, DMF was used as a reaction solvent and water was not added. Further, the reaction temperature of the fluoromethylation reaction was set at 65° C. The other operations were the same as Examples 1-1, 1-2 and 1-3 and the specific explanation is thus omitted.

Comparative Examples 2-1, 2-2 and 2-3

In Comparative Examples 2-1, 2-2 and 2-3, DMF was used as a reaction solvent and water was not added. Further, the reaction temperature of the fluoromethylation reaction was set at 90° C. The other operations were the same as Examples 1-1, 1-2 and 1-3 and the specific explanation is thus omitted.

Comparative Examples 3-1, 3-2 and 3-3

In Comparative Examples 3-1, 3-2 and 3-3, NMP was used as a reaction solvent and water was not added. Further, the reaction temperature of the fluoromethylation reaction was set at 90° C. The other operations were the same as Examples 1-1, 1-2 and 1-3 and the specific explanation is thus omitted.

Comparative Examples 4-1, 4-2 and 4-3

In Comparative Examples 4-1, 4-2 and 4-3, DMPU was used as a reaction solvent and water was not added. Further, the reaction temperature of the fluoromethylation reaction was set at 90° C. The other operations were the same as Examples 1-1, 1-2 and 1-3 and the specific explanation is thus omitted.

Comparative Examples 5-1, 5-2 and 5-3

In Comparative Examples 5-1, 5-2 and 5-3, DMPU was used as a reaction solvent and water was not added. Further, the reaction temperature of the fluoromethylation reaction was set at 120° C. The other operations were the same as Examples 1-1, 1-2 and 1-3 and the specific explanation is thus omitted.

Results of analyses made by rapid liquid chromatography in Examples 1-1 to 1-3, Examples 2-1 to 2-3, Comparative Examples 1-1 to 1-3, 2-1 to 2-3, 3-1 to 3-3, 4-1 to 4-3, and 5-1 to 5-3 are shown in FIGS. 3 to 9. In addition, reaction conditions in Examples 1 and 2 and Comparative Examples 1 to 5 and results of yields are shown in Table 1.

TABLE 1

| | Solvent | Reaction temperature (° C.) | Reaction time (min) | Yield of 2 (%) |
|---|---|---|---|---|
| Comparative Example 1-1 | DMF | 65 | 5 | 3 |
| Comparative Example 1-2 | DMF | 65 | 15 | 7 |
| Comparative Example 1-3 | DMF | 65 | 30 | 20 |
| Comparative Example 2-1 | DMF | 90 | 5 | 13 |
| Comparative Example 2-2 | DMF | 90 | 15 | 19 |
| Comparative Example 2-3 | DMF | 90 | 30 | 25 |
| Comparative Example 3-1 | NMP | 90 | 5 | 16 |
| Comparative Example 3-2 | NMP | 90 | 15 | 25 |
| Comparative Example 3-3 | NMP | 90 | 30 | 26 |
| Comparative Example 4-1 | DMPU | 90 | 5 | 27 |
| Comparative Example 4-2 | DMPU | 90 | 15 | 38 |
| Comparative Example 4-3 | DMPU | 90 | 30 | 40 |
| Comparative Example 5-1 | DMPU | 120 | 5 | 24 |
| Comparative Example 5-2 | DMPU | 120 | 15 | 26 |
| Comparative Example 5-3 | DMPU | 120 | 30 | 27 |
| Example 2-1 | DMPU:$H_2O$ (9:1) | 90 | 5 | 8 |
| Example 2-2 | DMPU:$H_2O$ (9:1) | 90 | 15 | 25 |
| Example 2-3 | DMPU:$H_2O$ (9:1) | 90 | 30 | 43 |
| Example 1-1 | DMPU:$H_2O$ (9:1) | 120 | 5 | 48 |
| Example 1-2 | DMPU:$H_2O$ (9:1) | 120 | 15 | 64 |
| Example 1-3 | DMPU:$H_2O$ (9:1) | 120 | 30 | 62 |

*A reaction was carried out by mixing [$^{18}$F]$FCH_2Br$ (ca. 0.5 GBq) and 1 (32 μmol) in a 0.5 mL of a solvent in the presence of $Pd_2(dba)_3$ (3.2 μmol), $P(o-CH_3C_6H_4)_3$ (19 μmol) and $K_2CO_3$ (3.6 μmol).
* The yield of the compound 2 was calculated from a peak area ratio of a [$^{18}$F] reaction generated product by analyzing the reaction solution in reversed HPLC. The yield is a mean value of two or three experiments. Note that when radioactivity amounts of the reaction solution were measured at reaction times of 5, 15 and 30 minutes in a reaction at 90° C. or 120° C., it was confirmed that [$^{18}$F]$FCH_2Br$ (boiling point at 17 to 18° C.) did not vaporize from the reaction solution.

It was found from FIGS. 3 to 9 that in a system in which water was added to an aprotic polar solvent, peak areas other than the raw material and the desired fluoromethylated product (2) are small and by-products are less generated as compared to a system in which no water was added.

For example, it was found as shown in FIG. 3 that in Examples 1-1 to 1-3 in which water was added to an aprotic polar solvent (see Table 1), [$^{18}$F]$FCH_2Br$ that is the fluorine source decreases with reaction times and the fluoromethylated product (2) that is a generated product increases, peak areas other than [$^{18}$F]$FCH_2Br$ and the desired fluoromethylated product (2) are small and by-products are less generated. On the other hand, in Comparative Examples 5-1 to 5-3 in which water was not added to an aprotic polar solvent, regardless of the same solvent, reaction temperature, and reaction time as in Examples 1-1 to 1-3 (see table 1), it was found as shown in FIG. 9 that peak areas other than [$^{18}$F]$FCH_2Br$ that is the fluorine source and the desired fluoromethylated product (2) are larger and by-products are apparently larger as compared to Examples 1-1 to 1-3.

Also in Examples 2-1 to 2-3 and Comparative Examples 4-1 to 4-3 in which a similar reaction was carried out at a reaction temperature of 90° C., it was found as shown in FIG. 4 and FIG. 8 that in Examples 2-1 to 2-3 in which water was added to an aprotic polar solvent, peak areas other than the raw material and the desired fluoromethylated product (2) are smaller and by-products are less generated as compared to Comparative Examples 4-1 to 4-3 in which no water was added.

Further, it was found that also in Comparative Examples 2 and 3 (FIGS. 6 and 7) in which no water was added to an aprotic polar solvent, signals other than [$^{18}$F]$FCH_2Br$ and the desired fluoromethylated product (2) are significantly observed and by-products are largely generated. It was also found that in Comparative Example 1 (FIG. 5), a large amount of [$^{18}$F]$FCH_2Br$ that is the fluorine source remained and the reaction did not sufficiently progress.

As shown in Table 1, as comparing yields of the desired generated products in Examples 1-1 to 1-3 in which water was added to an aprotic polar solvent and yields of the desired generated products in Comparative Examples 5-1 to 5-3 in which no water was added to an aprotic polar solvent, regardless of the same solvent, reaction temperature and reaction time in both of the examples and the comparative examples, Examples 1-1 to 1-3 showed higher yields in any reaction time.

In addition, the yield of Example 2-1 (the reaction time for 5 minutes) in which water was added to an aprotic polar solvent was 8%, which was a poor result as compared to the yield of Comparative Example 4-1 (the reaction time for 5 minutes) in which no water was added to an aprotic polar solvent in the same conditions. However, in the elapsed time from Example 2-2 (the reaction time for 15 minutes) to Example 2-3 (the reaction time for 30 minutes), yields increased from 25% to 43%, and by-products were also apparently less generated in Examples 2-1 to 2-3 than in Comparative Examples 4-1 to 4-3, as found in comparison between FIG. 4 and FIG. 8. It was found from the fact that in the method for rapid fluoromethylation of the present invention, extending the reaction time to a certain degree makes it possible to increase a yield and a purity even when a reaction temperature is low.

Further, as shown in FIG. 4, in Example 1-3 in which water was added to an aprotic polar solvent, the signal of [$^{18}$F]$FCH_2Br$ that is the fluorine source mostly disappeared in the reaction time for 30 minutes, and the large signal of the fluoromethylated product (2) that is the desired product appeared. It was found from this fact that the reaction completed in such a short time as from 15 minutes to 30 minutes and even when [$^{18}$F] has such a short half-life period as 110 minutes, the method in Example 1-3 can be favorably used as a method for preparation of a PET tracer.

In addition, fluoromethylation of methyl benzoate that is an aromatic compound was carried out in Examples 1-1 to 1-3 and Examples 2-1 to 2-3, and a fluoromethylation reaction can be carried out in the same manner also when an alkenyl compound and an alkynyl compound are used in place of an aromatic compound. The fact is obvious from specialists in this field from the viewpoint that the suzuki-miyaura cross coupling reaction having a wide acceptable range of a substrate is applied in the method for rapid fluoromethylation of the present invention.

Comparative Example 6

In Comparative Example 6, synthesis of p-[$^{18}$F]fluoromethyl benzoic acid methyl (2) was carried out using [$^{18}$F]FCH$_2$I as the fluorine source according to the following synthesis route (Formula 5). The details are shown below.

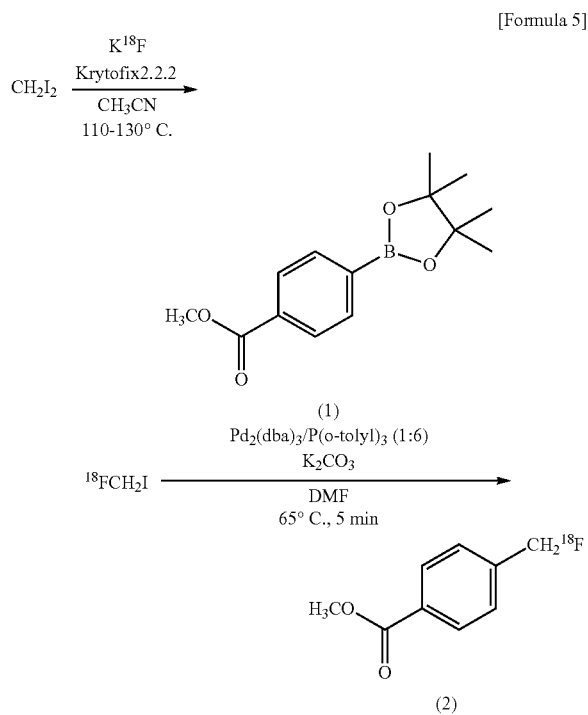

[Formula 5]

<Synthesis of [$^{18}$F]FCH$_2$I>

Synthesis of [$^{18}$F]FCH$_2$I that is the substrate of [$^{18}$F]fluoromethylation was carried out as follows using a labeling synthesis device (manufactured by Sumitomo Heavy Industries, Ltd.) shown in FIG. 10.

Water containing [$^{18}$F] fluorine ions was produced by irradiating 12 MeV electron beam (current value 30 μA, irradiation time 10 minutes) to [$^{18}$O] water (manufacture by TAIYO NIPPON SANSO CORPORATION, about 2 mL), using an accelerator cyclotron (HM-12S, manufactured by Sumitomo Heavy Industries, Ltd.) not shown. The aqueous [$^{18}$O] solution containing about 10 GBq of [$^{18}$F]fluorine ions thus obtained was transferred into the labeling synthesis device shown in FIG. 10, which was arranged in a hot cell not shown, and adsorbed to an anion exchange resin cartridge (Sep-Pak light Accell plus QMA Cartridges, manufactured by Waters). [$^{18}$F]KF was eluted into this cartridge through an aqueous acetonitrile solution (acetonitrile:water=700 μL:200 μL solution, 1 mL) containing Kryptofix 222 (K.222) (about 20 mg) and potassium carbonate (about 5 mg) and added to the primary reaction container. This solution was heated from 100 to 130° C. under reduced pressure with flowing a N$_2$ gas and solidified with drying. Subsequently, acetonitrile (1 mL) was added to azeotropically dry remaining water. An acetonitrile (0.6 mL) solution containing CH$_2$I$_2$ (about 50 μL) was added to the obtained residue, and [$^{18}$F]FCH$_2$I was synthesized with paying attention not to bumping under heating at 130° C. While the evaporated gas under the heating was pushed away with a N$_2$ gas, CH$_2$I$_2$ being the raw material, acetonitrile being the solvent, and the desired [$^{18}$F]FCH$_2$I were separated through a three-connected ion liquid vials (1-butyl-3-methylimidazolium trifluoromethanesulfonate 2 mL×2, 1-butyl-3-methylimidazolium bis(trifluoromethanesulfonyl)imide 1.5 mL×1). Almost all of CH$_2$I$_2$ being the raw material and acetonitrile being the solvent could be removed according to the operation. Note that the time for the serial operations of synthesis of [$^{18}$F]FCH$_2$I was about 40 minutes until separation and purification of [$^{18}$F]FCH$_2$I starting from supply of [$^{18}$F]F$^-$ from the cyclotron.

<Fluoromethylation Reaction>

Then, [$^{18}$F]FCH$_2$I (about 126 MBq: generally 100 to 300 MBq) was blown into 0.5 mL of a DMF solution that has been contained in the secondary reaction container in advance, and the obtained solution was transferred into the third reaction container containing the organoboron compound 1 (32 μmol), Pd$_2$(dba)$_3$ (3.2 μmol), P(o-CH$_3$C$_6$H$_4$)$_3$ (19 μmol), and K$_2$CO$_3$ (3.6 μmol) and reacted at 65° C. for 5 minutes.

A part of the reaction solution was extracted to carry out a HPLC analysis. As a result, as shown in FIG. 1, a HPLC analytical yield of the desired product 2 was as low as 23%, and peaks of by-products (indicated with small arrows) were large.

HPLC analysis conditions: COSMOSIL AR-II 4.6×150 mm column manufactured by NACALAI TESQUE, INC., column temperature at 30° C., eluate CH$_3$CN:H$_2$O=45:55, 1 mL/min flow rate, retention time of the desired product 2 for 6.5 to 7.5 minutes.

<PET Imaging>

A PET image of the compound (4) synthesized in Example 3 was taken. The details are described below.

0.1 mL of an aqueous 25% ascorbic acid solution was added to the solution separated in Example 3 and vacuum-concentrated using an evaporator. The concentrated liquid was diluted with a clinical administration solution (physiological saline: 2 mL, propylene glycol: 0.15 mL, Tween 80: 0.025 mL) and contained in a sterilized vial. The administration solution containing 38 MBq of the compound (4) was injected into a rat in the caudal vein and a PET image was taken.

Results are shown in FIG. 12. FIG. 12 shows the PET image of the entire body of the rat when 38 MBq of the compound (4) was administered in the caudal vein of the rat. As a result, accumulation into the brain was observed until 5 minutes after administration.

The invention should not be construed to be limited by description of the embodiments and examples of the invention described above at all. Various modified embodiments are also included in the invention within the range that a person skilled in the art can easily conceive of, without deviating from the scope of patent claims.

Figure 1:
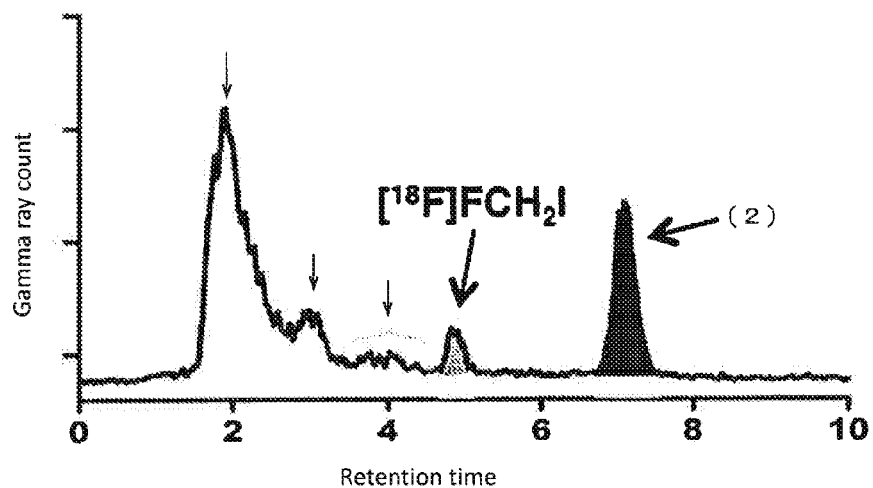
FIG. 1 shows a result of an analysis made by rapid liquid chromatography when FCH$_2$I is reacted by bonding to a benzene ring described in Patent Document 2 (Comparative Example 6).
Figure 2:
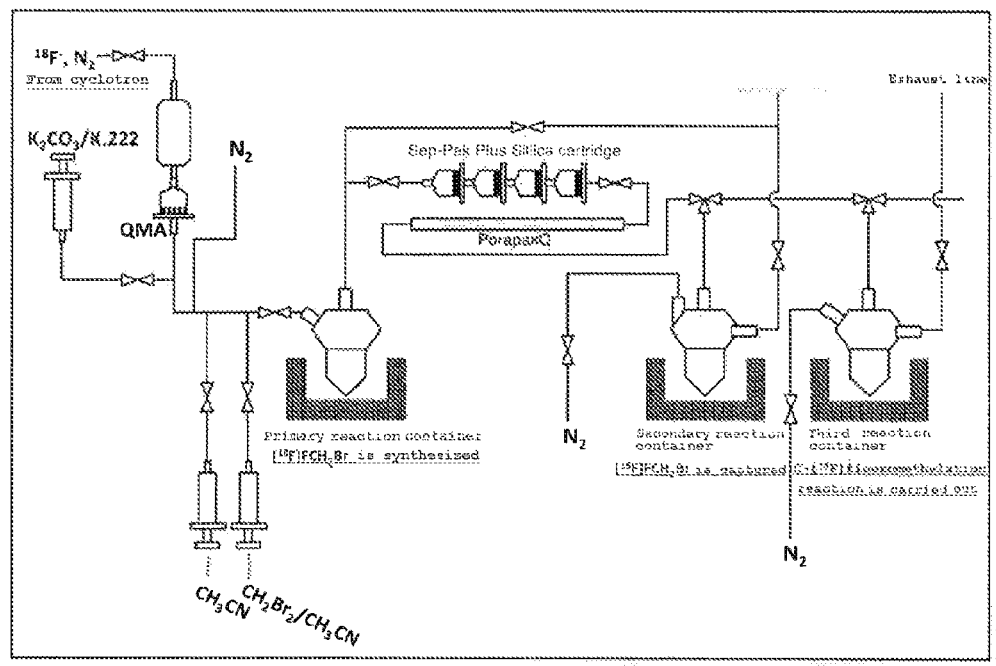
FIG. 2 is a schematic view showing synthesis of [$^{18}$F]FCH$_2$Br and a labeling synthesis device used for [$^{18}$F]fluoromethylation in Examples and Comparative Examples.
Figure 3:
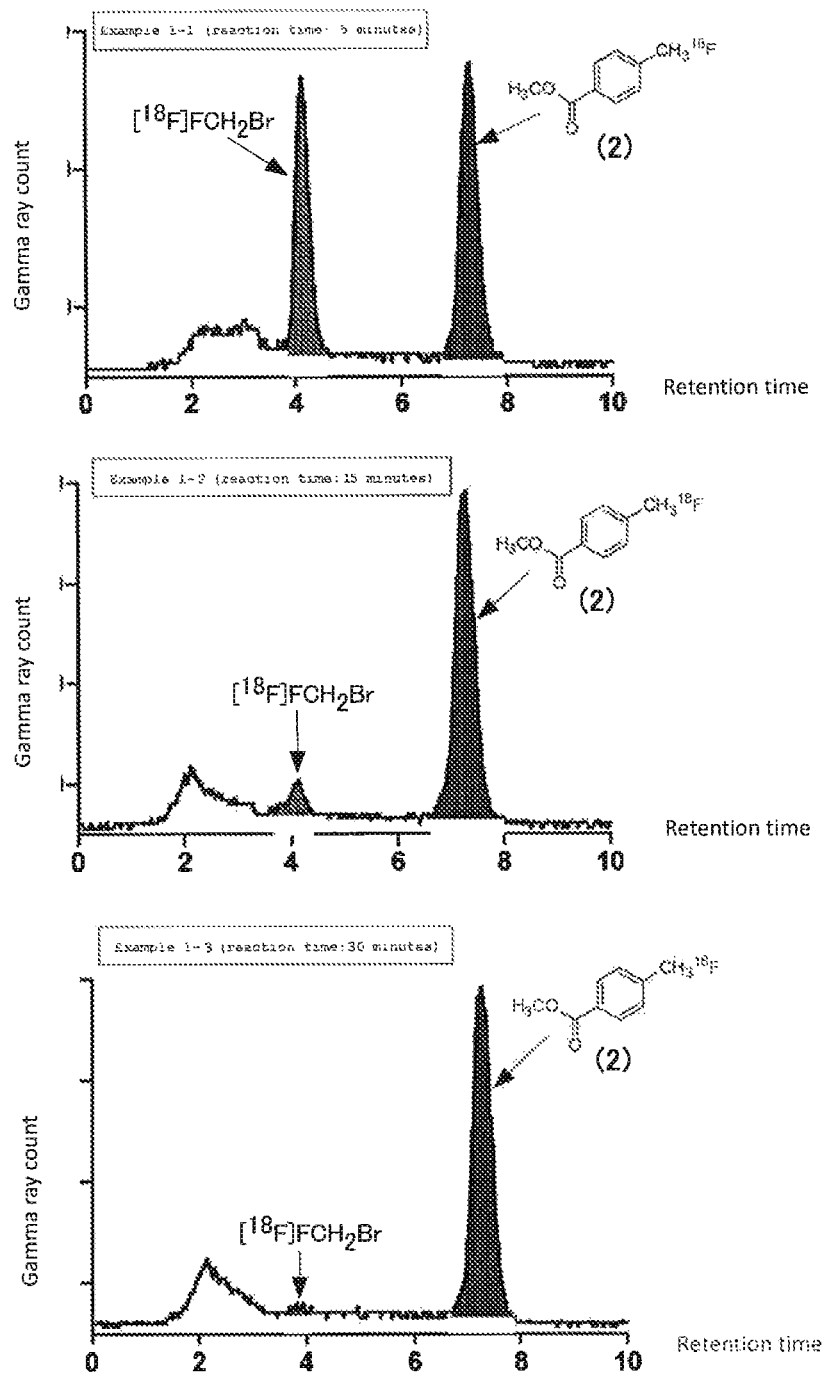
FIG. 3 shows results of analyses made by rapid liquid chromatography in Examples 1-1, 1-2 and 1-3.
Figure 4:
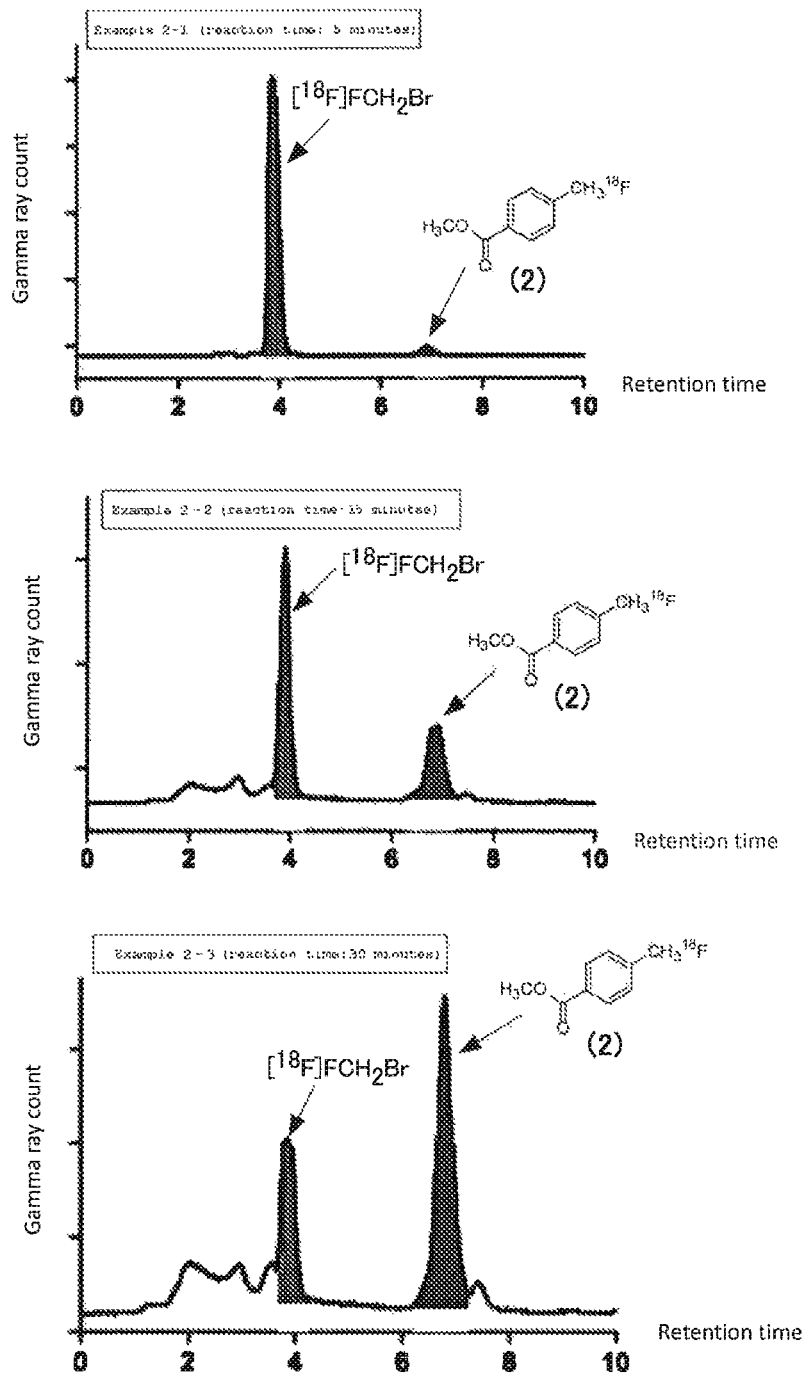
FIG. 4 shows results of analyses made by rapid liquid chromatography in Examples 2-1, 2-2 and 2-3.
Figure 5:
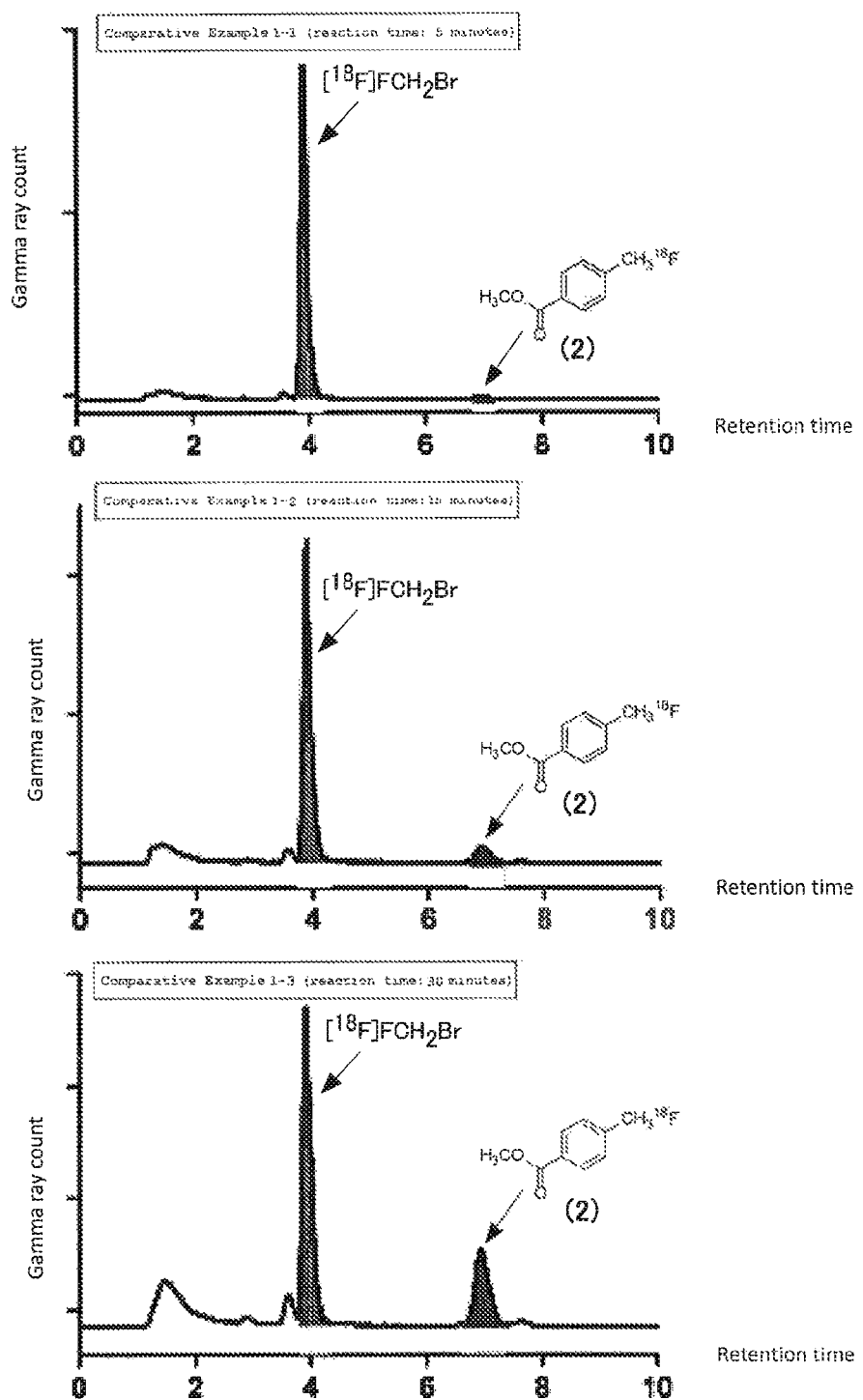
FIG. 5 shows results of analyses made by rapid liquid chromatography in Comparative Examples 1-1, 1-2 and 1-3.
Figure 6:
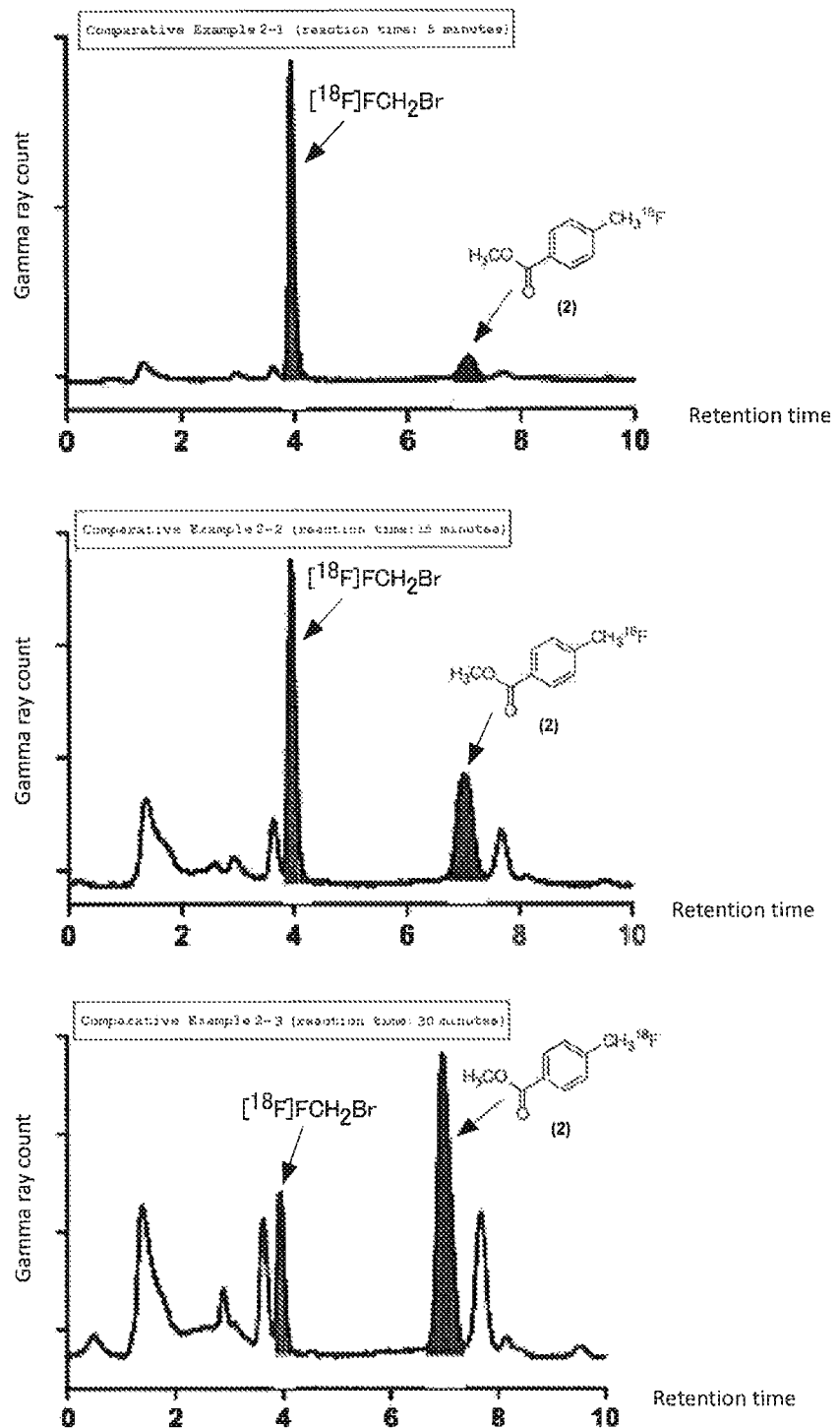
FIG. 6 shows results of analyses made by rapid liquid chromatography in Comparative Examples 2-1, 2-2 and 2-3.
Figure 7:
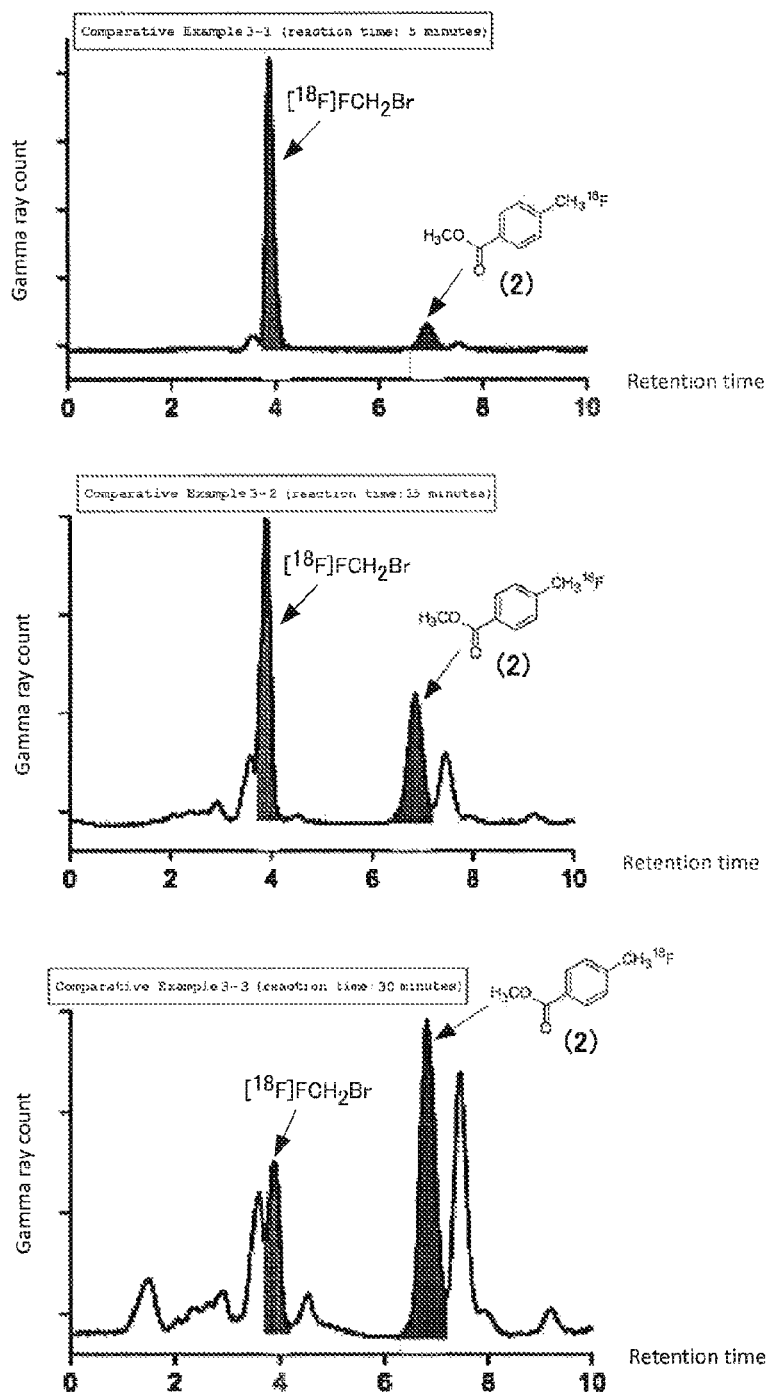
FIG. 7 shows results of analyses made by rapid liquid chromatography in Comparative Examples 3-1, 3-2 and 3-3.
Figure 8:
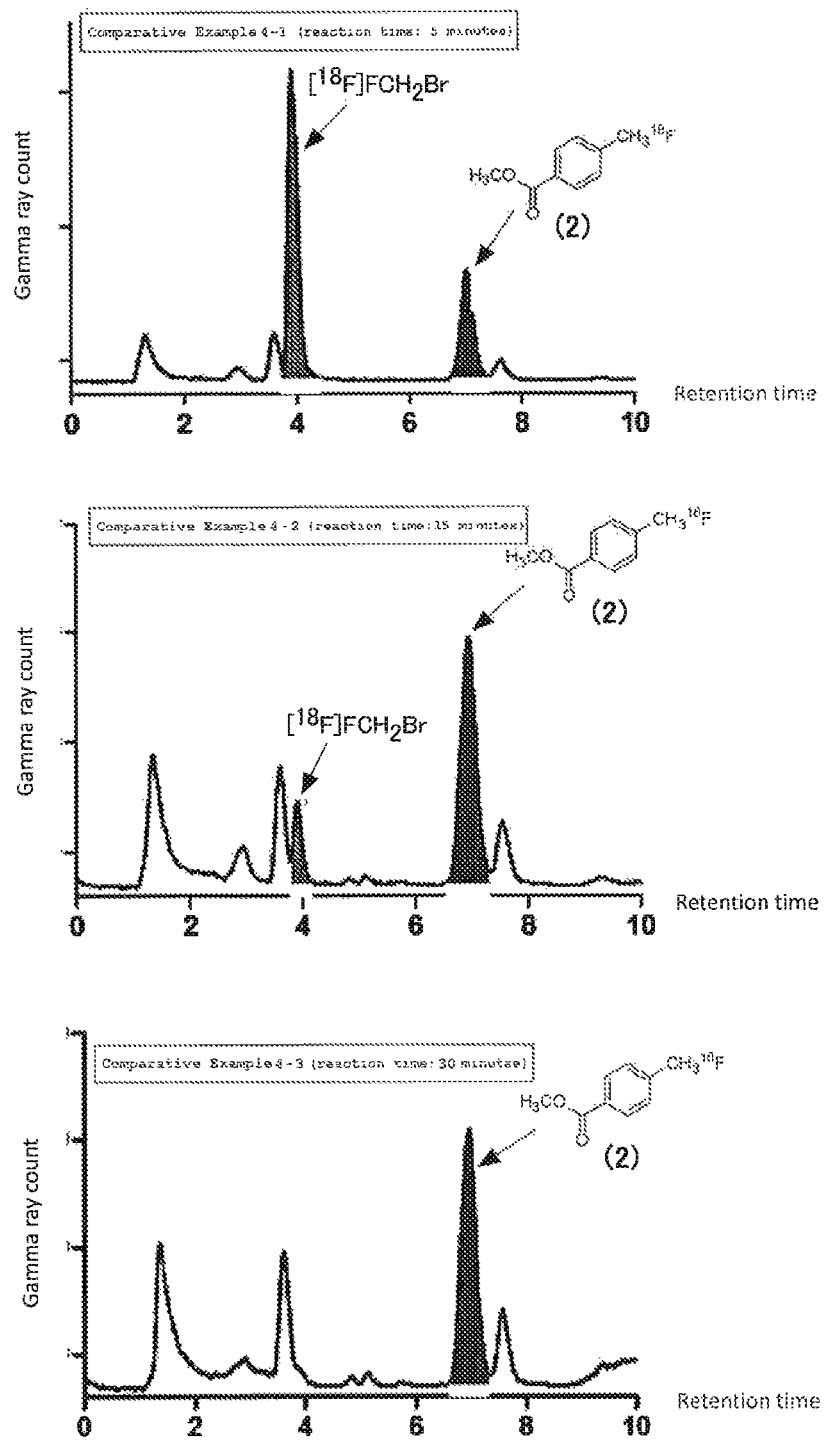
FIG. 8 shows results of analyses made by rapid liquid chromatography in Comparative Examples 4-1, 4-2 and 4-3.
Figure 9:
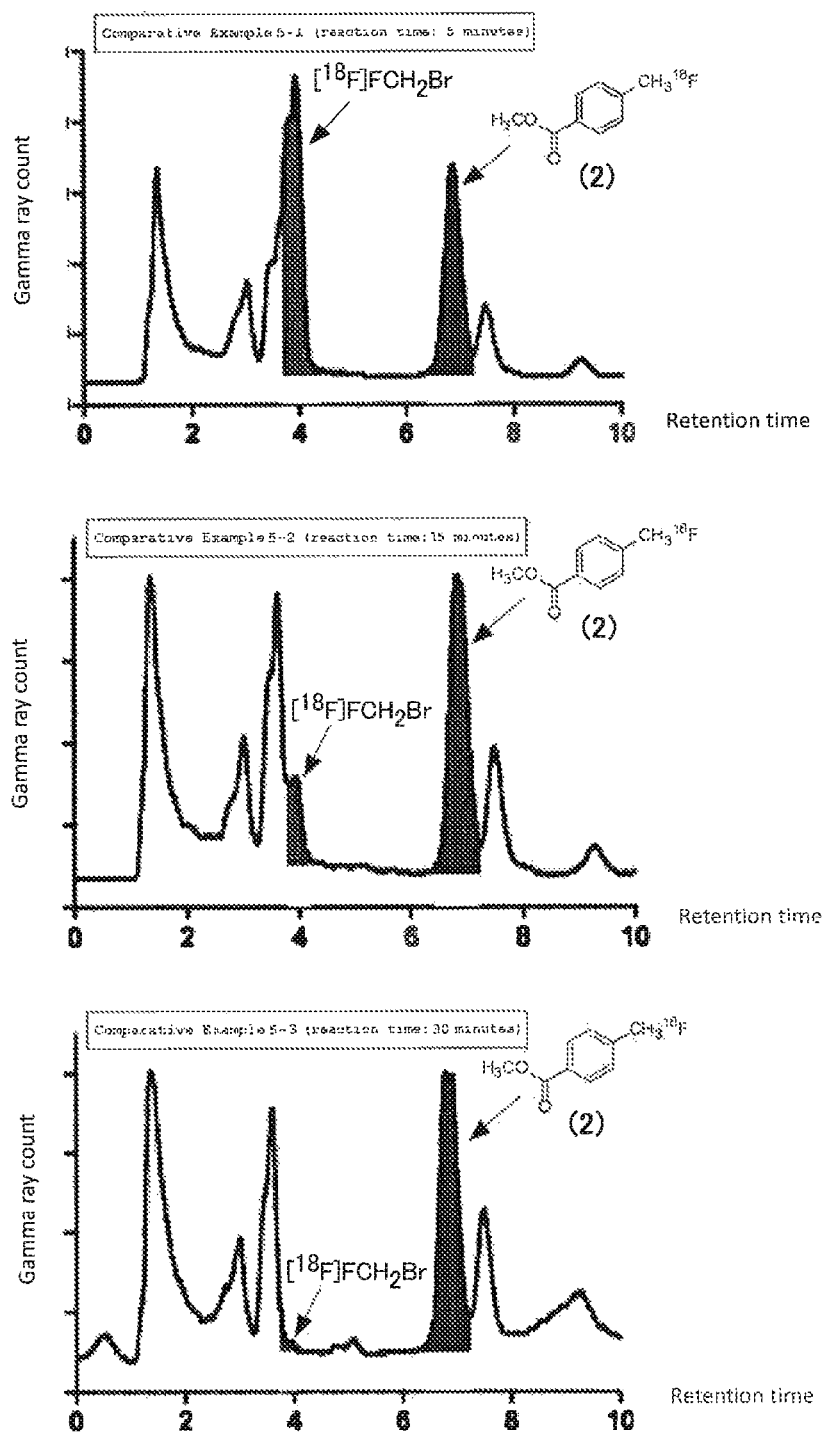
FIG. 9 shows results of analyses made by rapid liquid chromatography in Comparative Examples 5-1, 5-2 and 5-3.
Figure 10:
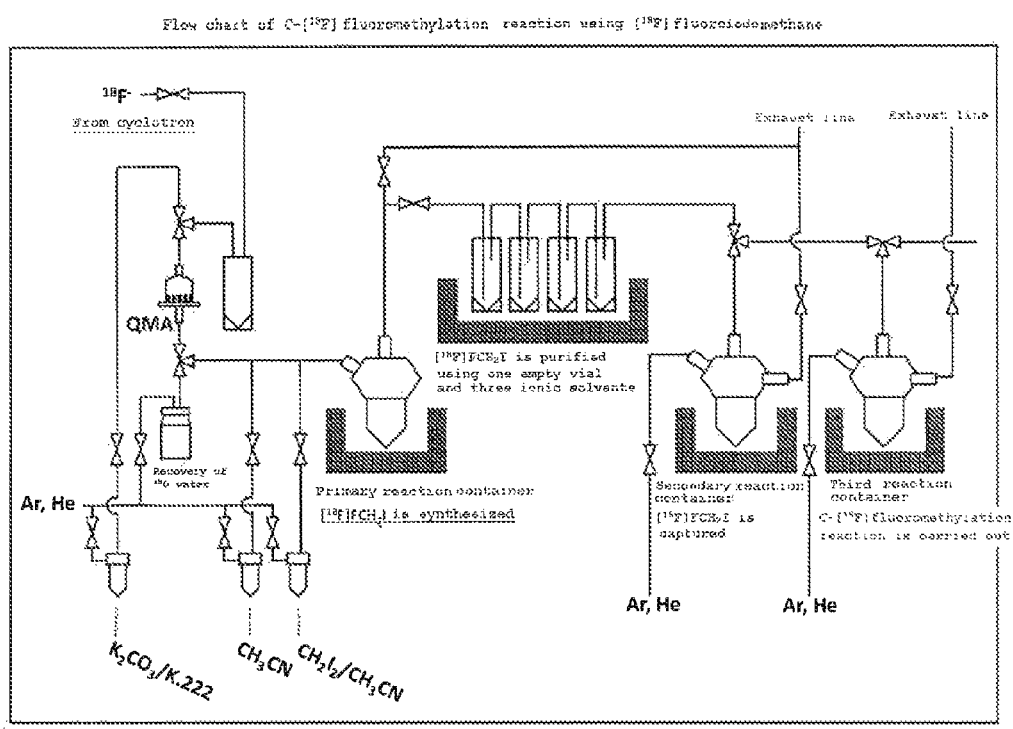
FIG. 10 is a schematic view showing synthesis of [$^{18}$F]FCH$_2$I and a labeling synthesis device used for [$^{18}$F]fluoromethylation in Comparative Example 6.
Figure 11:
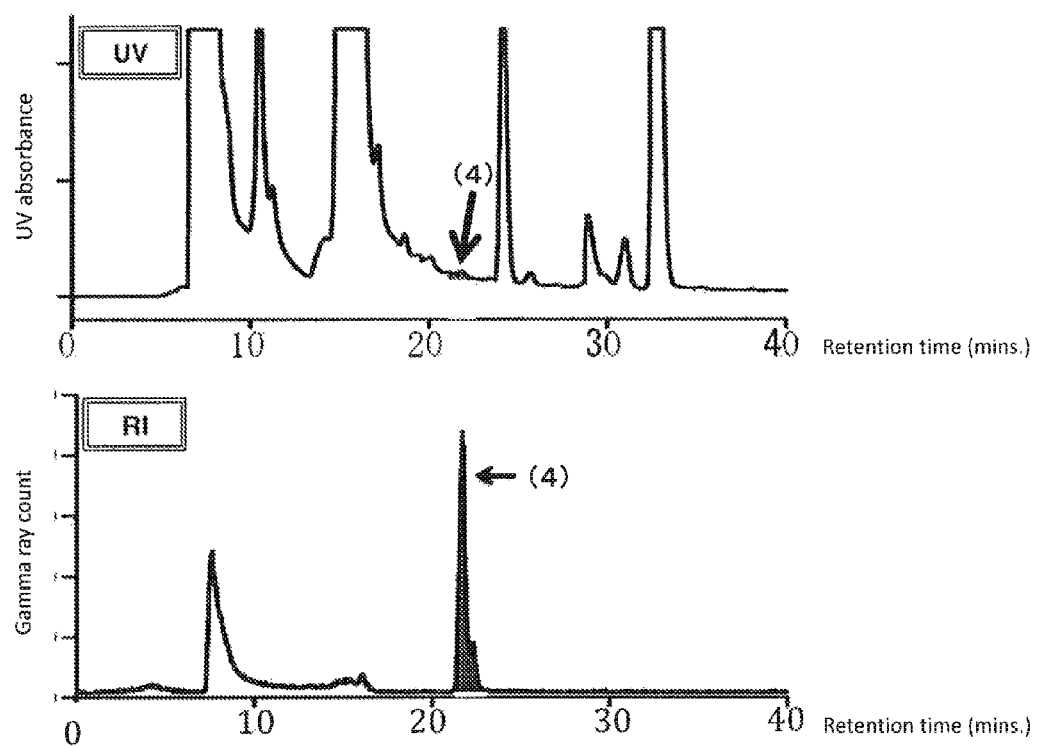
FIG. 11 shows a result of an analysis made by rapid liquid chromatography in Example 3.
Figure 12:
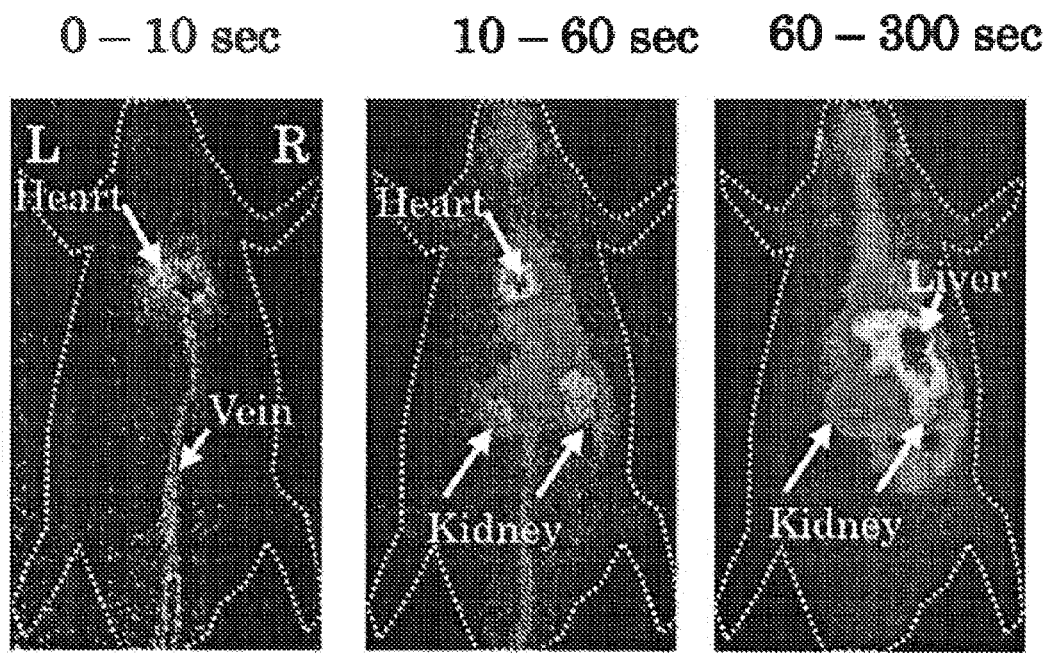
FIG. 12 shows a PET image of an entire body of a rat when the compound (4) synthesized in Example 3 was administered in caudal vein of the rat.

The invention claimed is:

1. A method for rapid fluoromethylation, wherein an organoboron compound in which an aromatic ring, an alkenyl group or an alkynyl group is bonded to a boron atom is cross-coupled with FCX$_2$Br (wherein X is ordinary hydrogen or heavy hydrogen) in the presence of a palladium complex, a phosphine ligand, and a base, in a solvent obtained by mixing water and N,N'-dimethylpropyleneurea, the reaction being performed at a temperature of from 90° C. to 120° C., and wherein the ratio of the volume of water to the volume of N,N'-dimethylpropyleneurea is in the range 0.05 to 0.15 inclusive.

2. The method for rapid fluoromethylation according to claim 1, wherein FCX$_2$Br is labeled with $^{18}$F.

3. The method for rapid fluoromethylation according to claim 1, wherein the organoboron compound in which an aromatic ring is bonded to a boron atom is a boronic acid ester.

4. The method for rapid fluoromethylation according to claim 1, wherein the base is a carbonate salt.

5. The method for rapid fluoromethylation according to claim 1, wherein the phosphine ligand is tri-o-tolylphosphine.

6. The method for rapid fluoromethylation according to claim 1, wherein the palladium complex is tris(dibenzylideneacetone)dipalladium(0).

7. The method for rapid fluoromethylation according to claim 1, wherein the palladium complex is tris(dibenzylideneacetone)dipalladium(0), and the phosphine ligand is tri-o-tolylphosphine.

8. The method for rapid fluoromethylation according to claim 1, wherein the palladium complex, the phosphine ligand, and the base are used in a molar equivalent amount or more with respect to FCX$_2$Br.

9. The method for rapid fluoromethylation according to claim 1, wherein the molar amount of the phosphine ligand used is twice or more with respect to the molar amount of Pd contained in the palladium complex.

10. A process for preparation of a PET tracer, wherein an organoboron compound in which an aromatic ring, an alkenyl group or an alkynyl group is bonded to a boron atom is cross-coupled with FCX$_2$Br (wherein X is ordinary hydrogen or heavy hydrogen) in the presence of a palladium complex, a phosphine ligand, and a base, in a solvent obtained by mixing water and N,N'-dimethylpropyleneurea, the reaction being performed at a temperature of from 90° C. to 120° C., and wherein the ratio of the volume of water to the volume of N,N'-dimethylpropyleneurea is in the range 0.05 to 0.15 inclusive.

11. The method for rapid fluoromethylation according to claim 2, wherein the organoboron compound in which an aromatic ring is bonded to a boron atom is a boronic acid ester.

12. The method for rapid fluoromethylation according to claim 2, wherein the base is a carbonate salt.

13. The method for rapid fluoromethylation according to claim 3, wherein the base is a carbonate salt.

14. The method for rapid fluoromethylation according to claim 2, wherein the phosphine ligand is tri-o-tolylphosphine.

15. The method for rapid fluoromethylation according to claim 3, wherein the phosphine ligand is tri-o-tolylphosphine.

16. The method for rapid fluoromethylation according to claim 1, wherein the organoboron compound is one in which an aromatic ring is bonded to a boron atom.

* * * * *